US006252119B1

(12) United States Patent
Salvador et al.

(10) Patent No.: US 6,252,119 B1
(45) Date of Patent: Jun. 26, 2001

(54) COPPER-CATALYSED ALLYLIC OXIDATION USING ALKYL HYDROPEROXIDE

(76) Inventors: Jorge António Riberiro Salvador, Av. Fernando Namora, 256-3°B, 3000 Coimbra (PT); Maria Luísa Campeão Fernandes Vaz de Sá e Melo, Rua Miguel Torga, Q$^{ta}$ dos Alpões, Lt 1-5°Esq, 3000 Coimbra (PT); André de Silva Campos Neves, Rua Condessa do Ameal, 53-3°, 3030 Coimbra (PT)

( * ) Notice: Subject to any disclaimer, the term of this patent is extended or adjusted under 35 U.S.C. 154(b) by 0 days.

(21) Appl. No.: 08/901,764

(22) Filed: Jul. 28, 1997

(51) Int. Cl.$^7$ .................................................. C07C 45/27
(52) U.S. Cl. ........................... 568/342; 568/349; 568/954; 568/955; 568/956
(58) Field of Search ..................................... 585/500, 523; 568/300, 303, 338, 408, 700, 314, 356, 951, 954, 955, 956

(56) References Cited

U.S. PATENT DOCUMENTS

| | | | |
|---|---|---|---|
| 3,914,295 | * 10/1975 | Rosenthal et al. | |
| 4,263,215 | 4/1981 | Hesse et al. | |
| 4,554,105 | 11/1985 | Hesse. | |
| 4,659,829 | * 4/1987 | Saussine et al. | 546/2 |
| 5,030,739 | 7/1991 | Foricher et al. | 552/542 |
| 5,296,481 | * 3/1994 | Partridge et al. | 514/178 |
| 5,354,919 | * 10/1994 | Costantini et al. | 568/432 |
| 5,457,111 | 10/1995 | Luly et al. | 514/291 |
| 5,585,371 | * 12/1996 | Lardy | 514/171 |
| 5,807,931 | * 9/1998 | Frechet | 525/333.3 |
| 5,869,709 | 2/1999 | Marwah et al. | 552/615 |

FOREIGN PATENT DOCUMENTS

| | | |
|---|---|---|
| WO 95/32215 | * 11/1995 | (WO). |
| WO 96/12810 | 5/1996 | (WO). |
| WO 97/37664 | 10/1997 | (WO). |

OTHER PUBLICATIONS

Lu et al, Journal of Molecular Catalysis, 70, pp. 391–7, 1991.*
Amann et al., "Stereospecific Syntheses of the Four Epimers of 7,22–Dihydorxycholesterol," Synthesis,pp. 1002–1005, Nov. 1987.*
Barton et al., "Metal Dependence in Gift–type Reactions. The Cu(II)–catalyzed Olefination of Saturated Hydrocarbons by tert–Butyl Hydorperoxide," Tetrahedron Letters, vol. 34, No.4, pp. 567–570, 1993.*
Cheng et al., "Chemistry and Biochemistry of Chinese Drugs. Part I. Sterol Derivatives Cytotoxic to Hepatoma Cells, Isolated from the Durg," J. Chem. Research. (s), pp. 217, 1977.*
Chidambram et al., "tert–Butyl Hydroperoxide–Prydinium Dichromate: A Convenient Reagent System for Allylic and Benzylic Oxidations, " J. Org. Chem,vol. 52, No. 22, pp. 5048–5051, 1987.*
Dauben et al., "Allylic Oxidation of Olefins with Chromium Trioxide–Pyridine Complex," J. of Org. Chem.,vol. 34, No. 11, pp. 3587–3592, Nov. 1969.*
Feldberg et al., "Copper–catalysed Oxidation of Hydroxy Compounds by tert–Butyl Hydroperoxide Under Phase – transfer Conditions," J. Chem. Soc., Chem. Commun.,pp. 1807, 1994.*
Fullerton et al., "In SituAllylic Oxidations with COllins Reagent," Synthetic Communications, Vol. 6, No. 3, pp. 217–220, 1976.*
Kimura et al., "On the Reaction of Cholesteryl Acetate with tert–Butyl Hydroperoxide in the Presence of Tris(acetylacetonato)iron(III), " Chem. Pharm. Bull., vol. 27, No.1, pp. 109–112, 1979.*
Kimura et al., "The Reactions of Cholesteryl Acetate with Various Hydroperxides in the Prescence of Tris(acetylacetonato)iron(III) and Hexacarbonylmolybdenum, " Chem. Pharm. Bull., Vol. 17, No. 1836–1841, 1980.*
Kumar et al., "Stereospecific Synthesis of 7β–and 7α–Hydroxycholesterols, " Synthetic Communications, vol. 17, No. 11, pp. 1279–1296, 1987.*
Marshall et al., "7–Keto Steroids. II. Steroidal 3β–Hydroxy–Δ5–7–ones and Δ3, 5–7–Ones," J. Am. Chem. Soc.,vol. 79, pp. 6308–6313, Dec. 5, 1957.*
Miller et al., "A Ruthenium Catalyzed Oxidation of Steroidal Alkenes to Enones, " Tetrahedron Letters, vol. 37, No. 20, pp. 3429–3432, 1996.*
Muzart,"Synthesis of Unsaturated Carbonyl Compounds via a Chromium–Mediated Allylic Oxidation by 70% Tert.Butylhydroperoxide," Tetrahedron Letters,vol. 28, No. 40, pp.4665–4668, 1987.*
Nagano et al., "Chemistry and Biochemistry of Chinese Drugs. Part II. Hydroxylated Sterols, Cytoxic towards Cancerous Cells: Synthesis and Testing, "J. Chem. Research (s), p. 218, 1977.*
Parish et al., "Allylic Oxidation of Δ5–Steroids with Pyridinium Chlorochromate (PCC) and Pyridinium Dichromate (PDC)," Synthetic Communications, vol. 17, No. 10, pp. 1227–1233, 1987.*
Parish et al., "Pyridium Chlorochromate–Mediated Allylic and Benzylic Oxidation, " Synthetic Communications, vol. 16, No. 11, pp. 1371–1375, 1986.*
Pearson et al., "A New Method for the Oxidation of Alkenes to Enones. An Efficient Synthesis of Δ5–7–Oxo Steroids," Chem. Soc. Perkin Trans. I, pp. 267–273, 1985.*
Pearson et al., "Oxidation of Alkenes to Enones Using tert–Butyl Hydroperoxide in the Presence of Chromium Carbonyl Catalysts," Tetrahedron Letters, vol. 25, No. 12, pp. 1235–1238, 1984.*

(List continued on next page.)

Primary Examiner—Jeffrey Mullis
(74) Attorney, Agent, or Firm—Michael S. Sherrill

(57) ABSTRACT

Δ5-7-oxo-steroids are efficiently prepared from Δ5-steroids using t-BuOOH in the presence of a copper catalyst, such as cuprous and cupric salts and copper metal.

8 Claims, No Drawings

OTHER PUBLICATIONS

Salmond et al., "Allylic Oxidation with 3,5-Dimethylpyrazole. Chromium Trioxide Complex. Steroidal Δ5-7-Ketones," *J. Org. Chem.,* vol. 43, No. 10, pp. 2057-2059, 1978.*

Sato et al., "Oxygenated Sterols as Inhibitors of Enzymatic Conversion of Dihydrolanosterol into Cholesterol," *Chem. Pharm. Bull.,* vol. 32, No. 8, pp. 3305-3308, 1984.*

Salvador et al Tetrahedron Lett. (1997) 38(1), p. 119-122, 1997.*

Kawasaki et al., Synlett, (12), p. 1245-6, 1995*

Zandervar et al., Tetrahedron: Asymetry, 7(7), p 1895-1898, Jul. 15,1996.*

Capdevielle, et al., CAPLUS AN 1990: 590457.*

"Dictionary of Steroids, Chemical Data, Structure and Bibliographies," *Chapman and Hall*, 1991, p. 267, 509.

Bulman Page et al., "Oxidation Adjacent to C=C Bonds," Comprehensive Organic Synthesis, vol. 7, Pergamon Press 1991, p. 83-84, 99-117.

Dodson et al., "Microbiological Transformations. IV. The Oxidation of Dehydroepiandrosterone at C-7," Dec. 5, 1959: 81, 6295-7.

Fieser, "Preparation of Ethylenethioketals," Apr. 5, 1954, 16: 1945-7.

Hudlicky, "Derivatives of Group 6 Elements," *Oxidations of Organic Chemistry*: 20-21.

Lardy et al., "Ergosteroids II: Biologically Active Metabolites and Sythetic Derivatives of Dehydroepiandrosterone," *Steroids*, Mar. 1998: 63(3): 158-65.

Marwah, "Steroidal Allylic Fluorination Using Diethylaminosulfur Trifluoride: A Convenient Method for the Synthesis of 3Beta-acetoxy-7 Alpha and 7Beta-fluoroandrost-5-en-17-one," *Steroids*, Aug. 1996: 61: 454-60.

Singh, "Phase-Transfer Catalysed Allylic Oxidation of Hindered Double Bonds in a Rigid Framework by Sodium Periodate," *Indian Journal of Chemistry*, Aug. 1985: 24B: 859.

* cited by examiner

COPPER-CATALYSED ALLYLIC OXIDATION USING ALKYL HYDROPEROXIDE

FIELD OF THE INVENTION

The invention relates to the allylic oxidation of organic compounds.

BACKGROUND

Allylic oxidation is a fundamental organic reaction of significant interest to organic chemists practicing in a variety of fields ranging from agricultural products to pharmaceuticals. A variety of procedures are known for allylically oxidizing various organic compounds. Unfortunately, such procedures typically suffer from unsatisfactory yields, tedious workups and/or require the use of expensive and/or ecologically and physiologically undesirable reagents.

Allylic oxidation reactions have traditionally been performed with chromium reagents, such as a $CrO_3$-pyridine complex, a mixture of chromium trioxide and 3,5-dimethylprazole, pyridinium chlorochromate (PCC), pyridinium dichromate (PDC), sodium chromate, or sodium dichromate in acetic acid. However, the great excess of reagent and the large volume of solvent required in such procedures, in combination with the difficult work-up required of the environmentally hazardous chromium residues, causes such procedures to be inconvenient for large scale production.

Of greater preparative interest has been the use of hydroperoxides with various catalysts to effect allylic oxidation. For example, the use of $Cro_3$ as a catalyst in the allylic oxidation of Δ5 steroids yields Δ5-7-ketones as the allylic oxidation product, along with minor quantities of a reaction product in which the double-bond is epoxidized. While good yields have been reported with hexacarbonyl chromium, $Cr(CO)_6$ pyridinium dichromate and $RuCl_3$ in the preparation of allylic oxidation products from Δ5-steroids, the toxicity of the chromium reagents and the high cost of the ruthenium catalyst renders commercialization of the procedures inconvenient.

Hence, a continuing need exists for a simple, efficient, safe and cost effective procedure for selectively effecting the allylic oxidation of organic compounds, particularly Δ5-steroids.

SUMMARY OF THE INVENTION

We have discovered a simple, efficient, safe, cost effective and ecologically friendly procedure for oxidizing organic compounds having allylic hydrogen atom(s). The procedure involves reactively contacting the organic compound with an alkyl hydroperoxide in the presence of a copper catalyst under conditions sufficient to effect oxidation of the allylic hydrogen(s) on the organic compound.

The reaction can conveniently be conducted at ambient pressure and elevated temperatures of approximately 50° to 70° C., and is conveniently conducted in a suitable organic solvent.

DETAILED DESCRIPTION OF THE INVENTION INCLUDING A BEST MODE

Definitions

As utilized herein, including the claims, the term "allylic compound" references an organic compound having at least one allylic hydrogen atom.

As utilized herein, including the claims, the term "allylic oxidation" means oxidation of an allylic compound by replacing the allylic hydrogen(s) with oxygen or an oxygen containing group.

As utilized herein, including the claims, the term "reactants" collectively references allylic substrates and alkyl hydroperoxide. Solvents, including both aqueous and organic solvents, and the copper catalyst are specifically excluded from the definition of reactants.

As utilized herein, including the claims, the term "wt %" means grams per 100 milliliters.

Process

The process involves reactively contacting an allylic compound with an alkyl hydroperoxide in the presence of a copper catalyst under conditions sufficient to effect allylic oxidation of the allylic hydrogen atom(s) on the organic compound.

CONSTITUENTS

Allylic Compounds

Allylic compounds include any organic compound incorporating the structure $—RC^1=C^2H—C^3H_n—$ within the molecule, wherein n is 1, 2 or 3. Hydrogen atoms attached to the $C^1$ and $C^2$ carbon atoms are referenced as vinylic hydrogen. Hydrogen atoms attached to the $C^3$ carbon atom are referenced as allylic hydrogen. The process of this invention selectively oxidizes allylic hydrogen atoms over vinylic hydrogen atoms. Exemplary allylic compounds include specifically, but not exclusively, (i) aliphatic vinylic compound such as methyl oleate, (ii) aromatic benzylic compounds such as fluorene and diphenyl methane, (iii) isoprenoids, such as carotenoids, terpenes, sesquiterpenes and vitamins, and (iv) steroids and sterols, such as androstenes, cholesterol, estraenes, pregnenes and derivatives thereof such as esters, ethers and ketals of these compounds.

Of particular commercial interest is the allylic oxidation of steroids, particularly Δ5 steroids such as dehydroepiandrosterone and derivatives of dehydroepiandrosterone, because such steroids possess pharmacological activity and can be allylically oxidized by the process of this invention without the use of physiologically or ecologically hazardous materials, such as the transition metals.

Oxidant (Alkyl Hydroperoxide)

An alkyl hydroperoxide is used to allylically oxidize an allylic compound in the presence of a copper catalyst. Experimentation has shown that butyl hydroperoxide, specifically t-butyl hydroperoxide, can generally provide a superior yield and/or superior quality of allylically oxidized product in accordance with the process of this invention. An additional benefit provided by the use of t-butyl hydroperoxide is that t-butyl hydroperoxide is a liquid under ambient conditions and can facilitate dissolution of the allylic compound in the organic solvent.

Alkyl hydroperoxide is available from a number of chemical suppliers. We have found anhydrous alkyl hydroperoxide to produce superior yields relative to aqueous solutions.

Generally, a concentration of about 4 to about 9 mole equivalents, preferably about 6 to about 7 mole equivalents, of alkyl hydroperoxide are effective for allylically oxidizing an allylic compound. Concentrations of less than about 4 mole equivalents of alkyl hydroperoxide significantly slows the reaction, while greater than about 9 mole equivalents of alkyl hydroperoxide increases the cost of the process without producing a corresponding increase in any beneficial property or characteristic of the process or resultant product(s).

Organic Solvent(s)

The organic reactants (i.e. allylic compound and alkyl hydroperoxide) and the copper catalyst are preferably dissolved in a suitable organic solvent. Selection of an organic solvent depends upon the specific allylic compound, alkyl hydroperoxide and copper catalyst used. A partial listing of suitable organic solvents includes specifically, but not exclusively; (i) water miscible solvents such as acetone, acetonitrile, and t-butanol, (ii) water immiscible solvents such as petroleum ether, n-hexane, n-heptane, iso-octane, benzene and cyclohexane, and (iii) organic bases such as pyridine. A preferred solvent for use in connection with most Δ5-Androstenes, such as dehydroepiandrosterone, is acetonitrile.

Copper Catalyst

Suitable copper catalysts effective for catalyzing the allylic oxidation in accordance with this invention include cuprous and cupric salts, and copper metal. Examples of suitable cuprous salts include specifically, but not exclusively, copper (I) oxide, copper (I) hydroxide, copper (I) chloride, copper (I) bromide, copper (I) iodide. Examples of suitable cupric salts include specifically, but not exclusively, copper (II) oxide, copper (II) sulfates, copper (II) chloride, copper (II) bromide, copper (II) iodide, copper (II) sulfide, copper (II) triflate. A particularly suitable copper metal is copper powder, such as available from Aldrich Chemicals. It is believed that the copper powder is transformed in situ into soluble copper compounds effective for catalyzing the allylic oxidation reaction.

PROCESSING PARAMETERS AND PROCEDURES

Reaction Time

While dependent upon a number of variables, including the specific allylic compound being oxidized, the specific alkyl hydroperoxide being used, the specific copper catalyst employed, and the concentration of reactants and catalyst within the reaction mixture, the reactions can typically be conducted in about 16 to about 24 hours.

Reaction Temperature

The reaction is preferably conducted at temperatures slightly above ambient (i.e., temperatures between about 50° to 70° C.). Temperatures below about 50° C. tend to slow the reaction rate without an observed increase in yield and/or quality of product, while temperatures above about 70° C. tend to reduce the yield and/or quality of desired oxidized product(s).

Mixing

The reaction mixture should be continuously and vigorously stirred in order to promote contact between the reactants and thereby speed-up the reaction time and enhance the yield and/or quality of the desired allylically oxidized organic compound.

Solvent Dilution Factor

As with any solvent-based reaction, the wt % solids should be retained between an upper solubility limiting percentage and a lower reaction rate limiting percentage. As the upper wt % of solids is reached, the viscosity of the resultant reaction mixture increases to such an extent that the necessary molecular interaction of the reactants are limited (e.g., the reaction mixture cannot be effectively mixed, with a resultant loss in yield and/or increased reaction time). Conversely, as the lower wt % of solids is reached, the reaction time begins to increase dramatically due to the reduced opportunity for the reactants to encounter one another within the reaction mixture. Such low concentrations of solids also results in increased expense due to the excessive amounts of solvent used per unit of reaction product obtained.

While the preferred wt % of solids in the reaction mixtures of this invention depend upon a number of variables, including the specific solvent(s) used and the specific reactants employed, a solids wt % of between about 4 to about 7 wt % has been found to be generally acceptable for producing a high yield of good quality product at a reasonable rate of reaction.

Separation and Purification Techniques

Upon completion of the oxidation reaction, the oxidized allylic organic compound can be separated from the solvent system, as well as any unused reactants and any byproducts, by any of a variety of techniques known to those skilled in the art including (i) dilution, (ii) filtration, (iii) extraction, (iv) evaporation, (v) distillation, (vi) decantation, (vii) crystallization/recrystallization, and/or (viii) chromatography.

Any excess alkyl hydroperoxide present in the reaction mixture upon completion of the reaction can be decomposed, as desired, by those methods known to those skilled in the art, such as (i) adding an aqueous solution of an alkali metal sulfite, (ii) adding a mixture of a mineral acid and acetic acid at a temperature of about 0° to 5° C., or (iii) adding a transition metal salt (e.g., ferrous ammonium sulfate) in water.

The isolated allylically oxidized product can be further purified by various known techniques such as (i) washing the isolated product with a solvent effective for selectively dissolving any remaining contaminants without dissolving appreciable quantities of the product, such as water or diethyl ether, and/or (ii) crystallizing the isolated product in a suitable solvent or cosolvent system.

EXAMPLES

Standard Protocol

An allylic substrate (1 mmole) is dissolved in an organic solvent (6 ml) and purged with nitrogen. A copper catalyst and t-butyl hydroperoxide are added to the solution and heated under constant agitation with a magnetic stirrer for a specified time period. The resultant solution is poured into a sodium sulfite solution (10% aq.) and extracted with diethyl ether. The extract is washed with an aqueous saturated solution of $NaHCO_3$, brine and water, dried over $MgSO_4$ and evaporated to dryness to yield an allylically oxidized product.

Examples 1–9

Various Δ5-steroids were allylically oxidized in accordance with the standard protocol set forth above utilizing the reagents, copper catalyst, solvent and processing parameters set forth in Table One below.

GLOSSARY
(Chemical Structure and Formula of Substrates)

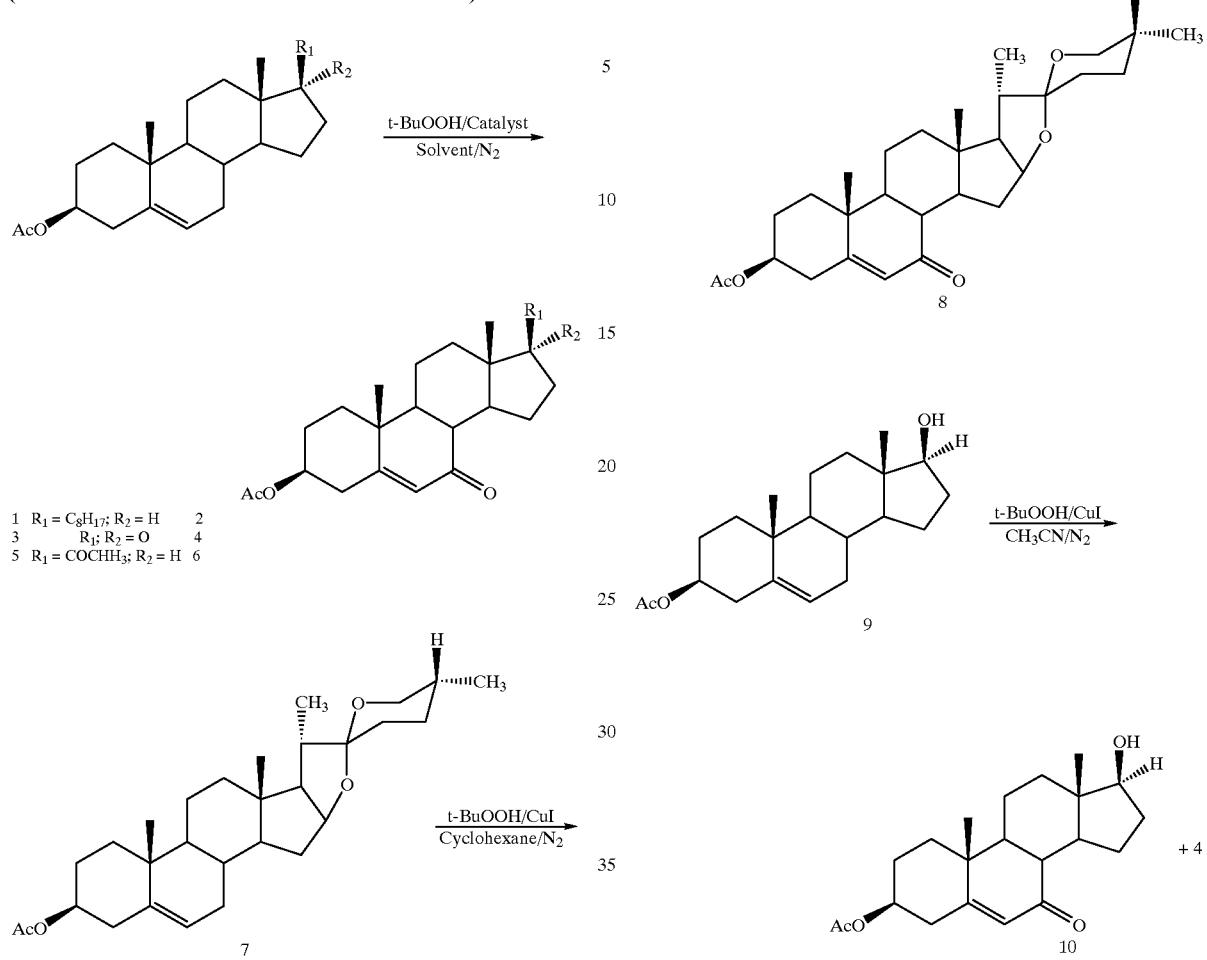

1 $R_1 = C_8H_{17}$; $R_2 = H$    2
3      $R_1$; $R_2 = O$    4
5 $R_1 = COCHH_3$; $R_2 = H$    6

TABLE ONE

ALLYLIC OXIDATION OF Δ5-STEROIDS

| Example | Substrate 1 mmole | t-BuOOH[a] (ml) | Catalyst | (mmoles) | Solvent | Time (h) | Temp. (° C.) | Prod. | Yield (%) |
|---|---|---|---|---|---|---|---|---|---|
| 1 | 1 | 1.2 | CuI | (0.026) | Benzene | 24 | 70 | 2 | 80[b] |
| 2 | 3 | 1.2 | CuI | (0.010) | CH$_3$CN | 20 | 50 | 4 | 83 |
| 3 | 3 | 1.2 | CuBr | (0.02) | CH$_3$CN | 25 | 55 | 4 | 80[c] |
| 4 | 3 | 1.2 | CuCl | (0.015) | CH$_3$CN | 18 | 55 | 4 | 81[c] |
| 5 | 3 | 1.2 | CuCl$_2$ | (0.02) | CH$_3$CN | 24 | 55 | 4 | 81[c] |
| 6 | 3 | 1.0 | Cu | (0.03) | CH$_3$CN | 16 | 50 | 4 | 84 |
| 7 | 5 | 1.2 | CuI | (0.007) | CH$_3$CN | 20 | 55 | 6 | 80[c] |
| 8 | 7 | 2.0 | CuI | (0.042) | Cyclohexane | 72 | 65 | 8 | 75[d] |
| 9 | 9 | 1.0 | CuI | (0.015) | CH$_3$CN | 24 | 50 | 10 | 70[e] |

[a]5.0–6.0M solution in decane (Aldrich)
[b]14% of starting material was recovered by flash chromatography (10% ethyl acetate in petroleum ether 40–60° C.).
[c]Traces of starting material and a by-product are visible on t.l.c. plates but not detectable in $^1$H-NMR spectrum (500 MHz) of the crude product.
[d]The crude product contains 10% of starting material, calculated on the basis of the $^1$H-NMR signal (6-H).
[e]Calculated on the basis of the $^1$H-NMR signal (6-H) of the crude product (10 + 4).

CONCLUSIONS AND OBSERVATIONS

The reaction performed on the Δ5-3β-acetoxy substrates 1, 3, 5 and 7 were very selective when compared with the use of t-BuOOH and Fe(acac)$_3$ as catalyst, as described in Kimura, M.; Muto, T. *Chem. Pharm. Bull.*, 1979, 27, 109 and Kimura, M.; Muto, T. *Chem. Pharm. Bull.*, 1980, 28, 1836, where the 7-ketone comes along with epimeric 7-alcohols and 7-alkylperoxides. It is noted that the replacement of Fe(acac)$_3$ with Mo(CO)$_6$ in this reaction has been also described, but leads to epoxidation of cholesteryl acetate with alkyl hydroperoxides in benzene. The same outcome is seen when Fe(acac)$_3$ catalyses the oxidative reactions with $H_2O_2$, with 5,6-epimeric epoxides constituting the major products.

We claim:

1. A process for effecting the allylic oxidation of a Δ5 androstene substituted at the 3 and 17 carbon positions comprising oxidizing the Δ5 androstene with an alkyl hydroperoxide in the presence of a copper catalyst so as to form an αβ unsaturated carbonyl compound as the predominant reaction product.

2. The process of claim 1 wherein the yield of α β usaturated carbonyl compound reaction product is at least 65% on a dry basis.

3. The process of claim 2 wherein the yield of α β unsaturated carbonyl compound reaction product is at least 70% on a dry basis.

4. The process of claim 2 wherein the yield of α β unsaturated carbonyl compound reaction product is at least 75% on a dry basis.

5. The process of claim 2 wherein the yield of α β unsaturated carbonyl compound reaction product is at least 80% on a dry basis.

6. The process of claim 1 wherein the copper catalyst is an inorganic copper salt or copper metal.

7. The process of claim 1 wherein the alkyl hydroperoxide is t-butyl hydroperoxide.

8. The process of claim 1 wherein the reaction is effected at a temperature of between about 50 to 70° C.

* * * * *